US009750404B2

(12) United States Patent
Tachikawa et al.

(10) Patent No.: US 9,750,404 B2
(45) Date of Patent: Sep. 5, 2017

(54) OPHTHALMIC IMAGING APPARATUS, CONTROL METHOD THEREFOR, AND NON-TRANSITORY COMPUTER-READABLE STORAGE MEDIUM

(71) Applicant: CANON KABUSHIKI KAISHA, Tokyo (JP)

(72) Inventors: Hiroto Tachikawa, Fujisawa (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 123 days.

(21) Appl. No.: 14/691,968

(22) Filed: Apr. 21, 2015

(65) Prior Publication Data
US 2015/0305617 A1    Oct. 29, 2015

(30) Foreign Application Priority Data

Apr. 28, 2014  (JP) ................. 2014-093168

(51) Int. Cl.
| A61B 3/14 | (2006.01) |
| A61B 3/10 | (2006.01) |
| A61B 3/12 | (2006.01) |
| A61B 3/00 | (2006.01) |
| A61B 3/113 | (2006.01) |

(52) U.S. Cl.
CPC ............ A61B 3/102 (2013.01); A61B 3/0041 (2013.01); A61B 3/113 (2013.01); A61B 3/1225 (2013.01); A61B 3/14 (2013.01)

(58) Field of Classification Search
CPC  A61B 3/102; A61B 3/14; A61B 3/113; A61B 3/0041; A61B 3/1225; G01B 9/02091; G01B 9/02064; G01B 9/02; G01B 9/02004; G01B 9/02067; G01N 21/4795

USPC ....... 351/205, 206, 208, 210, 213, 221, 246; 359/200.8, 205.1, 212.1, 619; 356/479; 606/4

See application file for complete search history.

(56) References Cited

U.S. PATENT DOCUMENTS

| 8,220,924 B2 | 7/2012 | Hanebuchi et al. |
| 8,919,959 B2 | 12/2014 | Makihira |
| 8,950,863 B2 | 2/2015 | Makihira |
| 8,992,018 B2 | 3/2015 | Makihira |
| 8,998,412 B2 | 4/2015 | Makihira |
| 9,044,166 B2 | 6/2015 | Murata et al. |

(Continued)

FOREIGN PATENT DOCUMENTS

| JP | 2011-215134 A | 10/2011 |
| JP | 2012-223264 A | 11/2012 |

*Primary Examiner* — Scott J Sugarman
*Assistant Examiner* — Mustak Choudhury
(74) *Attorney, Agent, or Firm* — Fitzpatrick, Cella, Harper & Scinto

(57) ABSTRACT

An ophthalmic imaging apparatus performs imaging to produce a tomographic image of a fundus of an examined eye based on interference light obtained by combining measurement light and reference light, determines whether aliasing has occurred in the tomographic image, when it is determined that the aliasing has occurred, moves a position in which an optical path length of the measurement light and an optical path length of the reference light match from a retina side to a choroid side of the examined eye, and generates a fundus image based on the tomographic image that has been produced through imaging in a state where the position has been moved to the choroid side.

22 Claims, 6 Drawing Sheets

(56) References Cited

U.S. PATENT DOCUMENTS

| | | |
|---|---|---|
| 9,055,891 B2 | 6/2015 | Suehira et al. |
| 2011/0228221 A1 | 9/2011 | Hanebuchi et al. |
| 2012/0002166 A1 | 1/2012 | Tomatsu et al. |
| 2012/0154747 A1 | 6/2012 | Makihira |
| 2012/0229764 A1 | 9/2012 | Tomatsu et al. |
| 2012/0281235 A1* | 11/2012 | Murata et al. ......... A61B 3/102 356/479 |
| 2013/0003074 A1* | 1/2013 | Kurosaka ................ G01B 9/02 356/479 |
| 2013/0070988 A1 | 3/2013 | Makihira |
| 2013/0182219 A1 | 7/2013 | Numajiri et al. |
| 2013/0215386 A1 | 8/2013 | Utagawa et al. |
| 2013/0215387 A1 | 8/2013 | Makihira et al. |
| 2013/0235342 A1 | 9/2013 | Makihira |
| 2014/0313479 A1 | 10/2014 | Nozato et al. |

\* cited by examiner

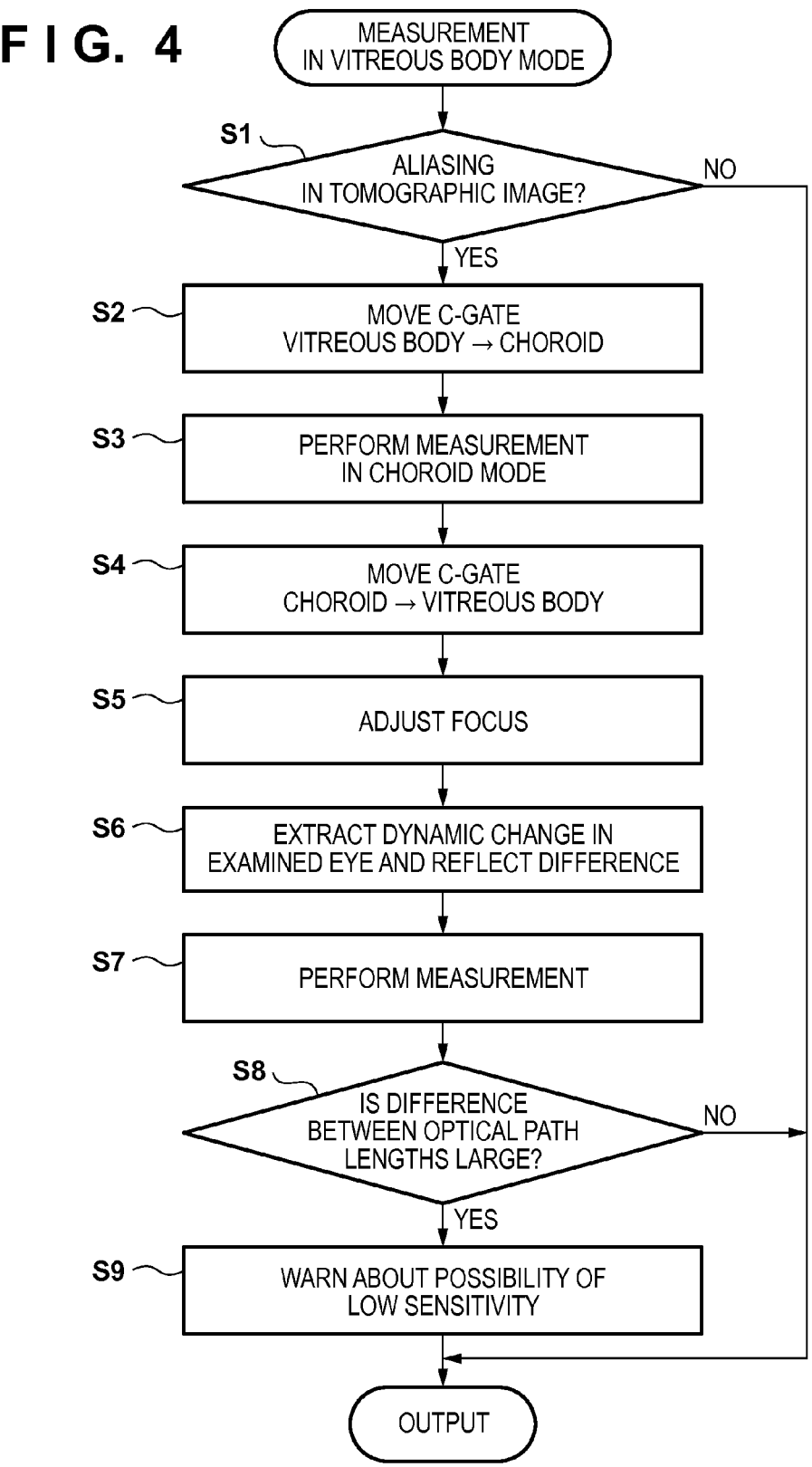

OPHTHALMIC IMAGING APPARATUS, CONTROL METHOD THEREFOR, AND NON-TRANSITORY COMPUTER-READABLE STORAGE MEDIUM

BACKGROUND OF THE INVENTION

Field of the Invention

The present invention relates to an imaging technique, and in particular to an ophthalmic imaging apparatus having an interference optics system used in, for example, an ophthalmic practice, a control method therefor, and a non-transitory computer-readable storage medium.

Description of the Related Art

Today, ophthalmic equipment provided with an optical device comes in a variety of forms. For example, various devices, such as an anterior ocular segment imaging device, a fundus camera, and a scanning laser ophthalmoscope (SLO), are used as optical devices for eye observation. In particular, an optical coherence tomography (OCT) apparatus (hereinafter referred to as an OCT apparatus) obtains high-resolution tomographic images of a specimen, and is emerging as essential ophthalmic equipment in the specialty of retinal medicine for outpatients.

The OCT apparatus performs high-sensitivity measurement by irradiating a sample (an object) with low-coherence light and utilizing reflected light from the sample and an interferometer. Furthermore, the OCT apparatus can obtain high-resolution tomographic images by scanning the entire sample irradiated with the low-coherence light. In this way, high-resolution tomographic images of the retina in the fundus of an examined eye can be produced through imaging. For the foregoing reasons, the OCT apparatus is widely used in, for example, ophthalmic diagnosis involving the retina.

Additionally, with the use of an apparatus incorporating the configurations of the OCT apparatus and the SLO, an examiner can perform imaging to produce a tomographic image of a desired segment while viewing a frontal fundus image of the examined eye (a fundus image). Meanwhile, a scheme is disclosed for generating a frontal fundus image based on the spectral intensity of an interference signal obtained by an OCT apparatus without incorporating the SLO configuration (Japanese Patent Laid-Open No. 2011-215134). Also, there is an apparatus that switches between OCT imaging modes in accordance with the depth of a segment to be imaged. This apparatus switches between a vitreous body mode and a choroid mode based on the distance from the position in which the optical path length of measurement light and the optical path length of reference light match to a predetermined boundary in a tomographic image of the fundus. In this way, a tomographic image of a vitreous body side and a tomographic image of a choroid side can be observed appropriately in the vitreous body mode and the choroid mode, respectively (Japanese Patent Laid-Open No. 2012-223264).

In recent years, as in Japanese Patent Laid-Open No. 2011-215134, there is an OCT apparatus which does not incorporate the SLO configuration and in which the horizontal width of a frontal fundus image on a display unit is set to be large relative to the horizontal width of an OCT image so as to display the frontal fundus image with an angle of view similar to that of a fundus camera. In general, a segment of interest in an OCT image is often the macula and the optic disc of the fundus. The shorter the distance from the position in which the optical path length of measurement light and the optical path length of reference light match (hereinafter, a coherence gate position) to an observed segment, the higher the sensitivity of the observed segment shown in a tomography image produced through imaging.

However, as the fundus has a curved shape, bringing the macula and the optic disc close to the coherence gate position could possibly cause a boundary between the posterior vitreous body and the retina to straddle the coherence gate position. In this state, a tomographic image undesirably shows an aliased image together with a real image in the vicinity of the coherence gate position. As a result, a frontal fundus image obtained based on luminance information of the tomographic image in a depth direction also shows an image abnormality in a ring-shaped region corresponding to an aliased portion.

SUMMARY OF THE INVENTION

In view of the above problems, the present invention provides a favorable image that is less influenced by an aliased image compared to conventional cases.

According to one aspect of the present invention, there is provided an ophthalmic imaging apparatus, which comprises: an imaging unit configured to perform imaging to produce a tomographic image of a fundus of an examined eye based on interference light obtained by combining measurement light and reference light; a determination unit configured to determine whether aliasing has occurred in the tomographic image; a movement unit configured to, when the determination unit has determined that the aliasing has occurred, move a position in which an optical path length of the measurement light and an optical path length of the reference light match from a retina side to a choroid side of the examined eye; and a generation unit configured to generate a fundus image based on the tomographic image that has been produced through imaging performed by the imaging unit in a state where the position has been moved by the movement unit to the choroid side.

Further features of the present invention will become apparent from the following description of exemplary embodiments (with reference to the attached drawings).

BRIEF DESCRIPTION OF THE DRAWINGS

FIG. 4 shows the flow from preliminary OCT measurement to main OCT measurement.

DESCRIPTION OF THE EMBODIMENTS

Figure 1:
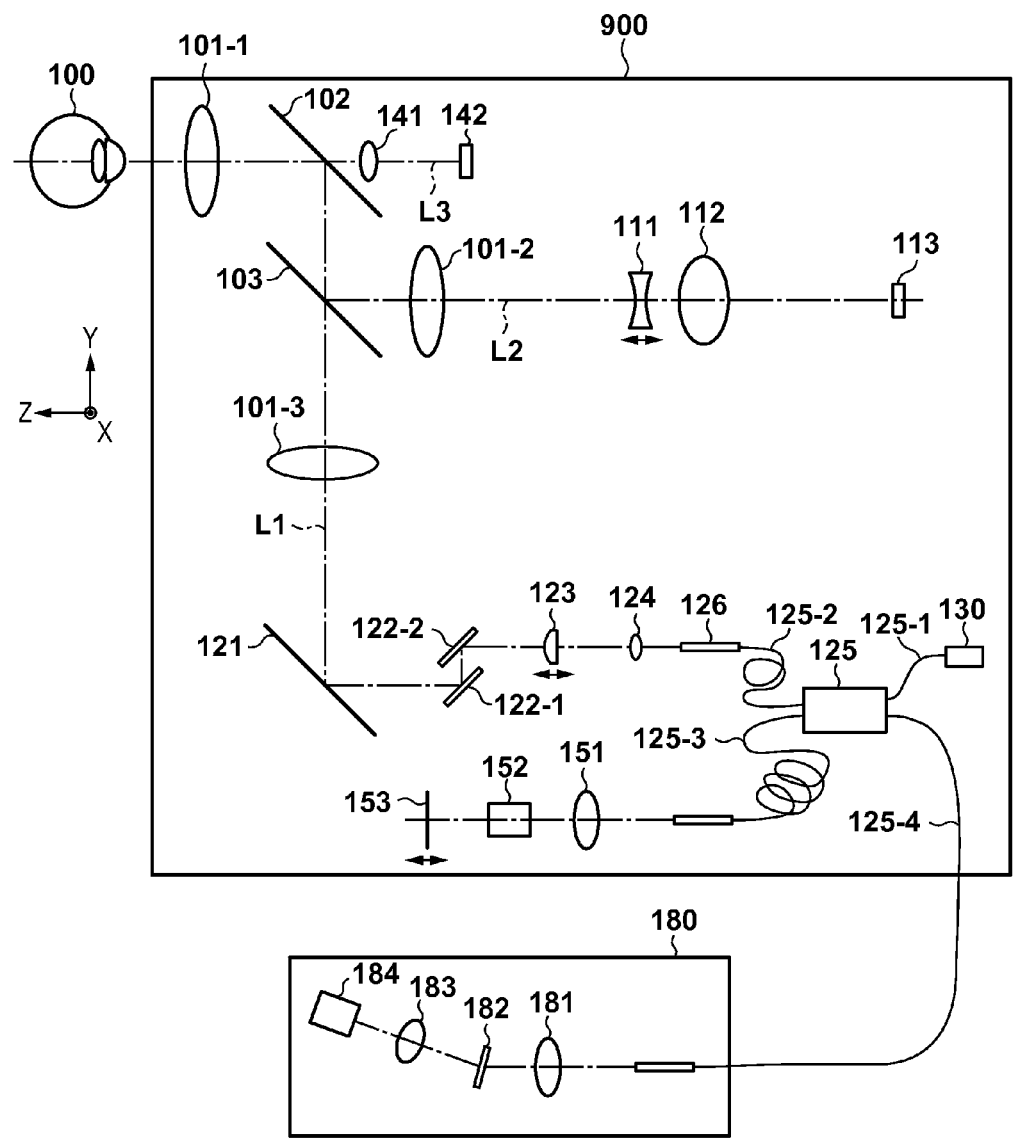
FIG. 1 shows a schematic configuration of an optical coherence tomography apparatus according to a first embodiment.

The following describes an embodiment of the present invention with reference to the attached drawings. It should be noted that, throughout the description, the same reference numeral indicates the same constituent.

(OCT Optics System)
<Apparatus Configuration>

FIG. 1 shows a schematic configuration of an optical coherence tomography apparatus (OCT apparatus) according to a first embodiment. The optical coherence tomography apparatus according to the present embodiment includes an optical head 900 and a spectrometer 180, and obtains a tomographic image of an object based on light obtained by combining return light from the object that has been irradiated with measurement light via scan units and reference light corresponding to the measurement light.

First, an internal configuration of the optical head 900 will be described. The optical head 900 is composed of a measurement optics system that performs imaging to produce an anterior ocular image and a tomographic image of an examined eye 100. An objective lens 101-1 is placed to oppose the examined eye 100, and an optical path is split on an optical axis of this lens by a first dichroic mirror 102 and a second dichroic mirror 103, which are optical path diverging units. That is to say, the optical path is split into the following optical paths corresponding to different wavelength bands: a measurement optical path L1 for the OCT optics system, an optical path L2 for fundus observation and a vision fixation lamp, and an optical path L3 for measurement of an anterior ocular segment.

Lenses 101-2, 111, 112 and a vision fixation lamp 113 are arranged on the optical path L2. Among the lenses 101-2, 111, and 112, the lens 111 is driven by an unillustrated motor for in-focus adjustment of the vision fixation lamp. The vision fixation lamp 113 facilitates vision fixation of an examinee by generating visual light. A lens 141 and an infrared CCD 142 for anterior ocular observation are arranged on the optical path L3. The infrared CCD 142 is sensitive to the wavelength of unillustrated irradiation light for anterior ocular observation, specifically, around 970 nm.

As stated earlier, the optical path L1 serves as a measurement optical path for the OCT optics system, and is used in performing imaging to produce a tomographic image of the fundus of the examined eye 100. More specifically, this optical path is used in obtaining an interference signal for forming a tomographic image. A lens 101-3, a mirror 121, and scan units, i.e., an X scanner 122-1 (first scan unit) and a Y scanner 122-2 (second scan unit) are arranged on the optical path L1. The X scanner 122-1 and the Y scanner 122-2 cause light to scan the fundus of the examined eye 100 in an X direction (main scanning direction) and a Y direction (sub scanning direction), which are respectively an example of a first direction and an example of a second direction intersecting with the first direction. It should be noted that, while the optical path between the X scanner 122-1 and the Y scanner 122-2 appears to be running in a direction parallel to a sheet surface of FIG. 1, this optical path actually runs in a direction perpendicular to the sheet surface.

Figure 2:
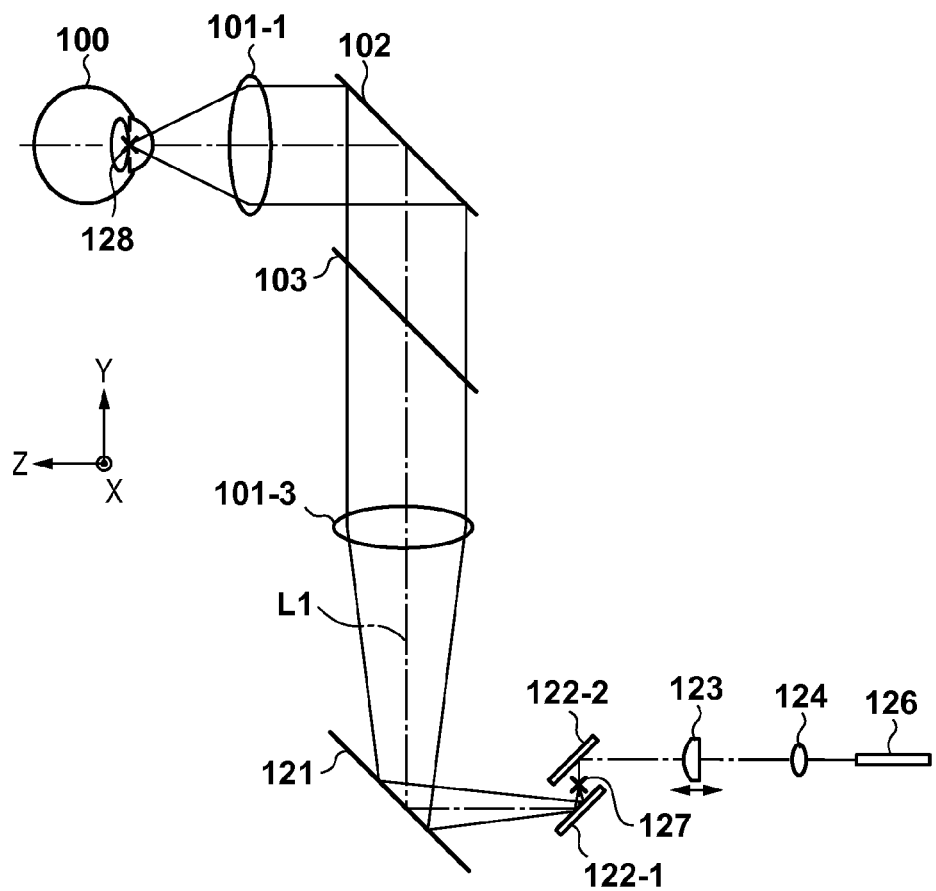
FIG. 2 shows a light flux incident on the pupil in the optical coherence tomography apparatus according to the first embodiment.

With reference to FIG. 2, the following describes detailed configurations on the optical path L1, a conjugate relationship associated with a pupil position on the optical path L1, and pencils from the pupil. FIG. 2 shows a light flux incident on the pupil in the optical coherence tomography apparatus according to the first embodiment. A position that is conjugate to a predetermined segment, such as the anterior ocular segment of the examined eye, is present between the X scanner 122-1 (first scan unit) and the Y scanner 122-2 (second scan unit). Therefore, in the present embodiment, a scanner center position 127, which is the center between the X scanner 122-1 and the Y scanner 122-2, is conjugate to a pupil position 128 of the examined eye 100.

Furthermore, the lens 101-1 (first lens), the lens 101-3 (second lens), and the X and Y scanners 122-1, 122-2 (or the scanner center position 127) are arranged such that pencils are substantially collimated between the lens 101-1 and the lens 101-3. According to this configuration, provided that measurement light deflection units (X scanner 122-1 and Y scanner 122-2) are object points, optical paths therefrom are substantially collimated between the lens 101-1 and the lens 101-3. In this way, when the X scanner 122-1 and the Y scanner 122-2 perform the scan, the angle of incidence on the first dichroic mirror 102 is the same as the angle of incidence on the second dichroic mirror 103. A measurement light source 126, which is a light source of the measurement light, makes the measurement light travel along the measurement optical path. In the present embodiment, the measurement light source 126 is an end of optical fibers 125-1 to 125-4 (FIG. 1), and is optically conjugate to a fundus segment of the examined eye 100.

Among lenses 123 and 124, the lens 123 is driven by an unillustrated motor in the directions indicated by a bidirectional arrow to perform in-focus adjustment. The in-focus adjustment is performed by adjusting light emitted by the measurement light source 126, which is the fiber end, such that the emitted light is formed on the fundus. In order to perform the in-focus adjustment, the lens 123 is arranged between the measurement light source 126 and the measurement light deflection units, i.e., the X scanner 122-1 and the Y scanner 122-2. In this way, there is no need to move the larger lens 101-3 and the optical fiber 125-2 connected to the measurement light source 126. This in-focus adjustment enables an image of the measurement light source 126 to be formed on the fundus of the examined eye 100, and enables return light from the fundus of the examined eye 100 to efficiently return to the optical fiber 125-2 via the measurement light source 126.

A description is now given of configurations of the optical paths of light emitted by a light source 130 shown in FIG. 1, a reference optics system, and the spectrometer 180. The light source 130, a mirror 153, a dispersion compensation glass 152, an optical coupler 125, the optical fibers 125-1 to 125-4, a lens 151, and the spectrometer 180 constitute a Michelson interferometer. The optical fibers 125-1 to 125-4 are single-mode optical fibers that are integrated together by way of connection to the optical coupler 125.

Light emitted by the light source 130 is divided into measurement light and reference light, which are emitted respectively toward the optical fiber 125-2 and the optical fiber 125-3, by the optical coupler 125 via the optical fiber 125-1. The measurement light irradiates an observation target, i.e., the fundus of the examined eye 100 via the above-described measurement optical path L1 for the OCT optics system, and then arrives at the optical coupler 125 via the same optical path as a result of reflection and scattering at the retina. On the other hand, the reference light arrives at and is reflected by the mirror 153 via the optical fiber 125-3, the lens 151, and the dispersion compensation glass 152 that is inserted to match dispersion of the measurement light with dispersion of the reference light. Then, the reference light travels back on the same optical path and arrives at the optical coupler 125.

The optical coupler 125 combines the measurement light and the reference light into interference light. Here, interference occurs when the optical path length of the measurement light and the optical path length of the reference light become substantially the same. The mirror 153 is held such that the position thereof can be adjusted by an unillustrated motor and driving mechanism in an optical axis direction, and can match the optical path length of the reference light with the optical path length of the measurement light that varies depending on the examined eye 100. The interference light is directed to the spectrometer 180 via the optical fiber 125-4.

The spectrometer 180 includes a lens 181, a diffraction grating 182, a lens 183, and a line sensor 184. After the interference light emitted by the optical fiber 125-4 is substantially collimated via the lens 181, the interference light is dispersed by the diffraction grating 182 and formed on the line sensor 184 by the lens 183.

The light source 130 will now be described. The light source 130 is a super luminescent diode (SLD), which is a typical low-coherence light source. It has a center wavelength of 855 nm and a wavelength bandwidth of approximately 100 nm. Here, the wavelength bandwidth is an important parameter as it influences the resolution of an obtained tomographic image in the optical axis direction. Furthermore, while the present embodiment adopts the SLD as a type of a light source, as it suffices to emit low-coherence light, amplified spontaneous emission (ASE) and the like can also be used. As measurement is performed with respect to the examined eye, near-infrared light is suitable in terms of the center wavelength. Furthermore, as the center wavelength influences the resolution of an obtained tomographic image in the horizontal direction, it is possible that the center wavelength be as short as possible. For these reasons, the center wavelength is set to 855 nm.

While the Michelson interferometer is used as the interferometer in the present embodiment, a Mach-Zehnder interferometer may be used. It is possible to use the Mach-Zehnder interferometer when a difference between a light amount of the measurement light and a light amount of the reference light is large, and to use the Michelson interferometer when the difference is relatively small.

<Imaging Method for Tomographic Image>

Figure 3:
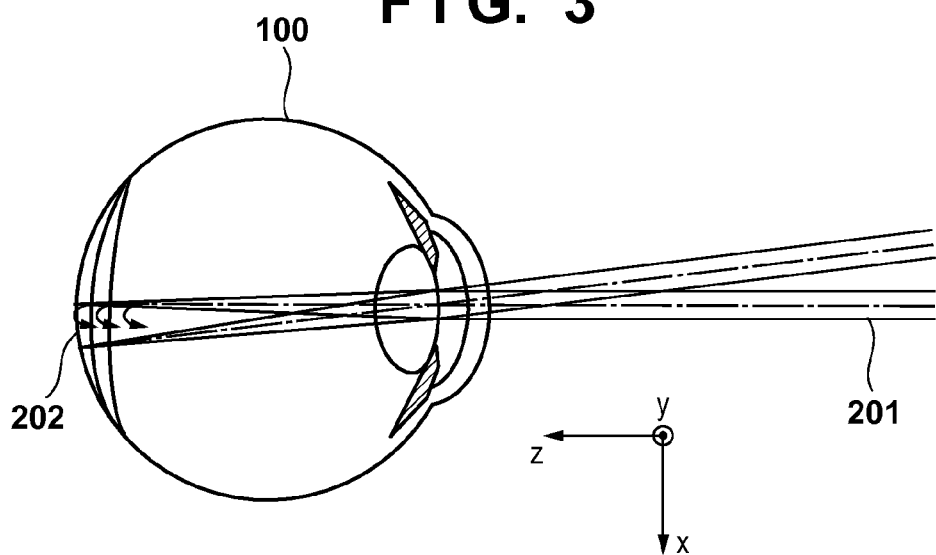
FIG. 3 shows scanning of an examined eye in an X direction.

The optical coherence tomography apparatus according to the present embodiment can perform imaging to produce a tomographic image of a desired segment in the fundus of the examined eye 100 by controlling the X scanner 122-1 and the Y scanner 122-2. FIG. 3 shows how the optical coherence tomography apparatus irradiates the examined eye 100 with measurement light 201 and scans a fundus 202 in the X direction. The optical coherence tomography apparatus images information corresponding to a predetermined number of images, from within an imaging range of the fundus 202 in the X direction, using the line sensor 184 of the spectrometer 180. The optical coherence tomography apparatus applies fast Fourier transform (FFT) to a luminance distribution on the line sensor 184 obtained at a predetermined position in the X direction, and converts the linear luminance distribution obtained as a result of FFT into an image with density or color information to display the same on a monitor. This converted image is referred to as an A-scan image. A two-dimensional (X direction x Z direction) image obtained by arraying a plurality of A-scan images is referred to as a B-scan image (tomographic image). The optical coherence tomography apparatus can obtain a plurality of B-scan images by, after a plurality of A-scan images for constructing one B-scan image have been produced through imaging, moving a scan position in the Y direction and then performing the scan again in the X direction. The optical coherence tomography apparatus displays a plurality of B-scan images or a three-dimensional tomographic image constructed from the plurality of B-scan images on a display unit, i.e., the monitor; in this way, the examiner can make a diagnosis from the examined eye using the displayed image(s).

<Vitreous Body Mode and Choroid Mode>

The optical coherence tomography apparatus according to the present embodiment has the vitreous body mode and the choroid mode related to the position of the mirror 153, and hence can switch between OCT imaging modes in accordance with a segment to be imaged. The optical coherence tomography apparatus switches between the vitreous body mode and the choroid mode based on the distance from the aforementioned position in which the optical path length of the measurement light and the optical path length of the reference light match (the coherence gate position) to a predetermined boundary in a tomographic image of the fundus. In the vitreous body mode, the optical coherence tomography apparatus positions the mirror 153 such that the coherence gate position is at a vitreous body side of the fundus. In this way, the optical coherence tomography apparatus can observe the vicinity of the posterior vitreous body with high sensitivity. On the other hand, in the choroid mode, the optical coherence tomography apparatus positions the mirror 153 such that the coherence gate position is at a choroid side. As a result, a displayed tomographic image is reversed in the up-down direction compared to the case of the vitreous body mode.

<Method for Generating Frontal Fundus Image>

A description is now given of a method for generating a frontal fundus image. In the following description, it will be assumed that an OCT image of the examinee is obtained in the vitreous body mode at first. FIG. 4 shows a processing sequence from when measurement is performed in the vitreous body mode to when the frontal fundus image is generated. An A-scan image is a tomographic image in the depth direction (Z direction) at one point on the fundus of the examined eye, and is composed of a plurality of pieces of luminance information in the depth direction. For example, the optical coherence tomography apparatus according to the present embodiment uses the line sensor 184 having 2048 pixels, and an A-scan image Ai to which Fourier transform has been applied is composed of 1176 pieces of luminance information. Here, P0 denotes luminance information of the shallowest portion in the depth direction, and P1175 denotes luminance information of the deepest portion in the depth direction. The optical coherence tomography apparatus according to the present embodiment obtains a representative magnitude signal at one point on the fundus of the examined eye by selectively extracting one of this plurality of pieces of luminance information. The following describes a method for obtaining the representative magnitude signal.

First, the optical coherence tomography apparatus rearranges pieces of luminance information P0 to P1175 of one target A-scan image in descending order of magnitude of luminance, that is to say, into R0 to R1175. Here, R0 denotes a pixel having the brightest luminance information, and R1175 denotes a pixel having the darkest luminance information. The optical coherence tomography apparatus selects a pixel Rx of a predetermined rank from among R0 to R1175. Here, the pixel of the predetermined rank is the $x^{th}$ pixel from the beginning among pixels that have been rearranged in descending order of magnitude of luminance information. As most of the pixels composing a tomographic image of the retina are dark pixels, it is possible that x be the pixel that is ranked in the top half of the total number of pixels. For example, in the case where an A-scan image composed of a total of 1176 pixels is used, the optical coherence tomography apparatus can obtain luminance information appropriate for a magnitude image by selecting the 118$^{th}$ pixel from the beginning, which is ranked in the top 10%, as the pixel Rx of the predetermined rank.

The optical coherence tomography apparatus decides on the luminance information of the pixel Rx of the predetermined rank as magnitude information of one target A-scan image. Then, the optical coherence tomography apparatus decides on magnitude information for every single A-scan image that has been produced through imaging, thereby obtaining pieces of magnitude information in one-to-one correspondence with different points on the examined eye 100. The optical coherence tomography apparatus can obtain a frontal fundus image of the examined eye by recomposing these pieces of magnitude information as a two-dimensional image. This planar image is similar to a fundus image obtained with other fundus cameras and SLOs, and enables pseudo visualization of the surface of the fundus. Furthermore, as the optical coherence tomography apparatus selectively obtains only one piece of luminance information from among a plurality of pieces of luminance information, the optical coherence tomography apparatus can obtain an appropriate planar image without being influenced by noise components contained in the A-scan images.

<Determination about Aliasing in Tomographic Image>

Referring to FIG. 4, in step S1, the optical coherence tomography apparatus determines whether to display a tomographic image (B-scan image) obtained in the vitreous body mode and a frontal fundus image obtained based on luminance information of that tomographic image in the depth direction (hereinafter referred to as aliasing determination). The aliasing determination is performed based on whether a boundary in a fundus layer structure straddles the position in which the optical path length of the measurement light and the optical path length of the reference light match (coherence gate position). As the fundus has a curved shape, bringing the macula and the optic disc close to the coherence gate position could possibly cause a boundary between the posterior vitreous body and the retina to straddle the coherence gate position. This state possibly could lead to the occurrence of a phenomenon in which a tomographic image undesirably shows an aliased image (also referred to as a folded image, a mirror image) together with a real image in the vicinity of the coherence gate position. This phenomenon is hereinafter referred to as aliasing (also referred to as folding). As a result of the occurrence of aliasing, a frontal fundus image obtained based on luminance information of the tomographic image in the depth direction also shows an image abnormality in a ring-shaped region corresponding to an aliased portion.

A frontal fundus image displayed by the optical coherence tomography apparatus according to the present embodiment has a smaller horizontal width than a tomographic image displayed by the same. This is because while the optical coherence tomography apparatus displays a region in which the vicinity of the macula and the optic disc can be observed as a tomographic image, it displays a region similar to that of a fundus camera as a frontal fundus image. Therefore, even if aliasing has not occurred in a displayed tomographic image, a frontal fundus image could possibly show a ring image with an abnormal portion. In view of this, the optical coherence tomography apparatus determines whether aliasing has occurred throughout the length of the horizontal width of a frontal fundus image. If the result of this determination suggests that imaging can be performed without aliasing, the optical coherence tomography apparatus displays the obtained tomographic image and frontal fundus image. On the other hand, if aliasing occurs, the optical coherence tomography apparatus changes the position of the mirror 153 so as to move the coherence gate position in the vitreous body mode to the coherence gate position in the choroid mode in step S2. It should be noted that this movement may be implemented automatically.

<Coherence Gate Movement 1 (from Vitreous Body Mode to Choroid Mode)>

Figure 5A:
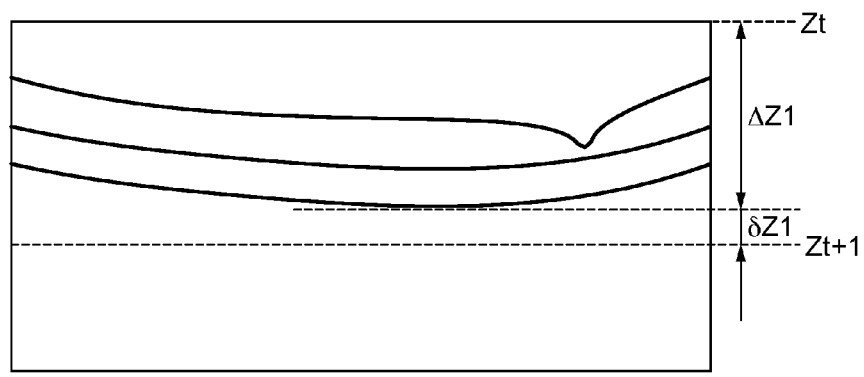
FIGS. 5A and 5B show the amount of movement of a coherence gate position (from a vitreous body mode to a choroid mode).
Figure 5B:
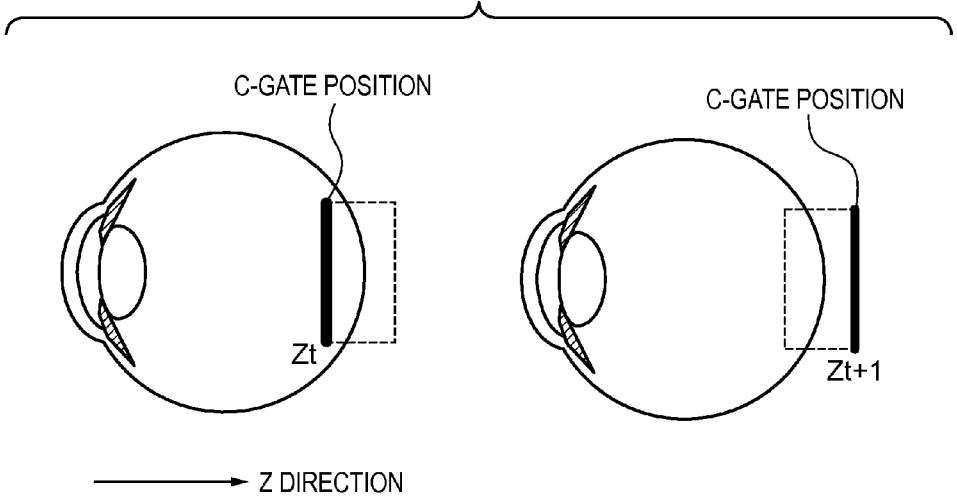

The amount of movement of the coherence gate position from a current position is calculated based on a tomographic image (B-scan image) obtained in the above-described manner. FIGS. 5A and 5B are diagrams for describing the amount of movement of the coherence gate position from the vitreous body mode to the choroid mode. As shown in FIGS. 5A and 5B, the optical coherence tomography apparatus moves the coherence gate position in the vitreous body mode, Zt, by a distance that is equal to a sum of a distance to an outer boundary portion of the choroid in the tomographic image, $\Delta Z1$, and a margin $\delta Z1$ so as to reach the coherence gate position in the choroid mode, Zt+1.

<Obtainment of Frontal Fundus Image in Choroid Mode>

In step S3, the optical coherence tomography apparatus obtains a frontal fundus image by performing OCT imaging in the choroid mode. At this time, scanning is performed with the X scanner 122-1 and the Y scanner 122-2 such that the scan width in the X direction and the scan width in the Y direction are larger than the size of the frontal fundus image to be displayed on the monitor at the time of preview (from step S5 to step S7). The optical coherence tomography apparatus adds margins to Lx and Ly, which are the lengths of the frontal fundus image to be displayed on the monitor in the X direction and the Y direction, to obtain the scan widths of Lx+$\Delta$Lx and Ly+$\Delta$Ly in step S3. In this way, the optical coherence tomography apparatus can select an area of the frontal fundus image to be displayed on the monitor in accordance with the amount of a later-described involuntary fine motion of the examined eye. Furthermore, in step S3, the optical coherence tomography apparatus samples data for obtaining a B-scan image at a higher density by performing the scan with the X scanner 122-1 and the Y scanner 122-2 at a speed lower than the speed at the time of preview. As a result, a high-definition frontal fundus image can be obtained. The optical coherence tomography apparatus stores the obtained frontal fundus image into a memory (not shown).

<Coherence Gate Movement 2 (from Choroid Mode to Vitreous Body Mode)>

In step S4, the optical coherence tomography apparatus moves the coherence gate position again, this time from the coherence gate position in the choroid mode to the coherence gate position in the vitreous body mode. It should be noted that this movement may be implemented automatically. The optical coherence tomography apparatus calculates the amount of this movement from the OCT image produced through imaging in step S3. By calculating the optimal amount of movement, the optical coherence tomography apparatus can obtain a tomographic image with a favorable sensitivity and also prevent a measurement error. In general OCT measurement, the smaller the difference between the optical path of the measurement light and the optical path of the reference light, the higher the sensitivity of the obtained tomographic image. That is to say, in the vitreous body mode, a high-sensitivity tomographic image can be obtained in the state where an observed segment has moved to a position close to the upper end of the tomographic image. However, when the B-scan width (the scan width in the X direction or the scan width in the Y direction)

is large, obtaining a tomographic image without aliasing in consideration of the curve of a fundus surface will naturally increase the distance from the coherence gate position to the boundary between the vitreous body and the retina, which could possibly reduce the sensitivity of a segment of interest (the macula and the optic disc) in the tomographic image. This is because the difference between the optical path of the measurement light and the optical path of the reference light ultimately increases, ending up with being influenced by the roll-off characteristics. In view of the above, the optical coherence tomography apparatus moves the coherence gate position in consideration of the curve of the fundus; this makes it possible to obtain a tomographic image with a favorable sensitivity.

Figure 6A:
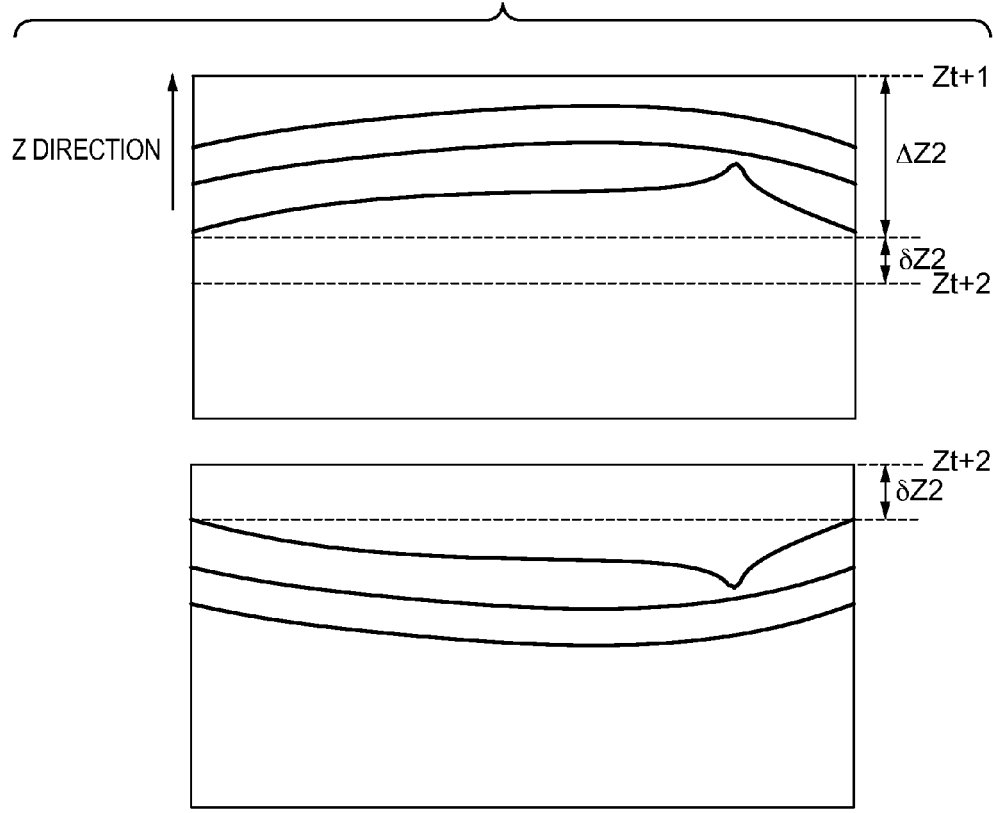
FIGS. 6A and 6B show the amount of movement of the coherence gate position (from the vitreous body mode to the choroid mode).
Figure 6B:
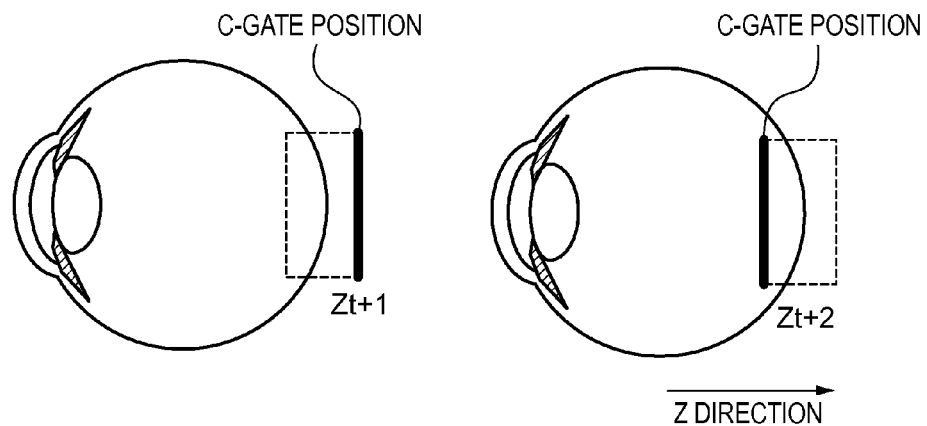

FIGS. 6A and 6B are diagrams for describing the amount of movement of a current coherence gate position in the choroid mode to the coherence gate position in the vitreous body mode. As stated earlier, a tomographic image displayed in the choroid mode is reversed in the up-down direction compared to the case of the vitreous body mode. As shown in FIGS. 6A and 6B, when the coherence gate position at the time of imaging in the choroid mode is $Z_{t+1}$ and the distance from the coherence gate position (the upper end of the tomographic image) to a boundary portion between the vitreous body and the retina is $\Delta Z2$, the coherence gate position in the vitreous body mode, $Z_{t+2}$, is obtained by $(Z_{t+1})+\Delta Z2+\delta Z2$. The coherence gate position and an OCT image in the choroid mode are shown. It should be noted that $\delta Z2$ denotes a margin from the coherence gate position to the boundary position between the vitreous body and the retina. When there is no $\delta Z2$, there is a possibility that aliasing occurs in the tomographic image due to an involuntary fine motion of the examined eye, and tone adjustment for the tomographic image cannot be appropriately performed due to extremely high luminance at the boundary portion. In view of this, the margin $\delta Z2$ is added at the time of calculation of the coherence gate position so as to avoid the foregoing defects and prevent a reduction in throughput of measurement.

<Display of Frontal Fundus Image and Focus Adjustment on Preview Screen>

Figure 7:
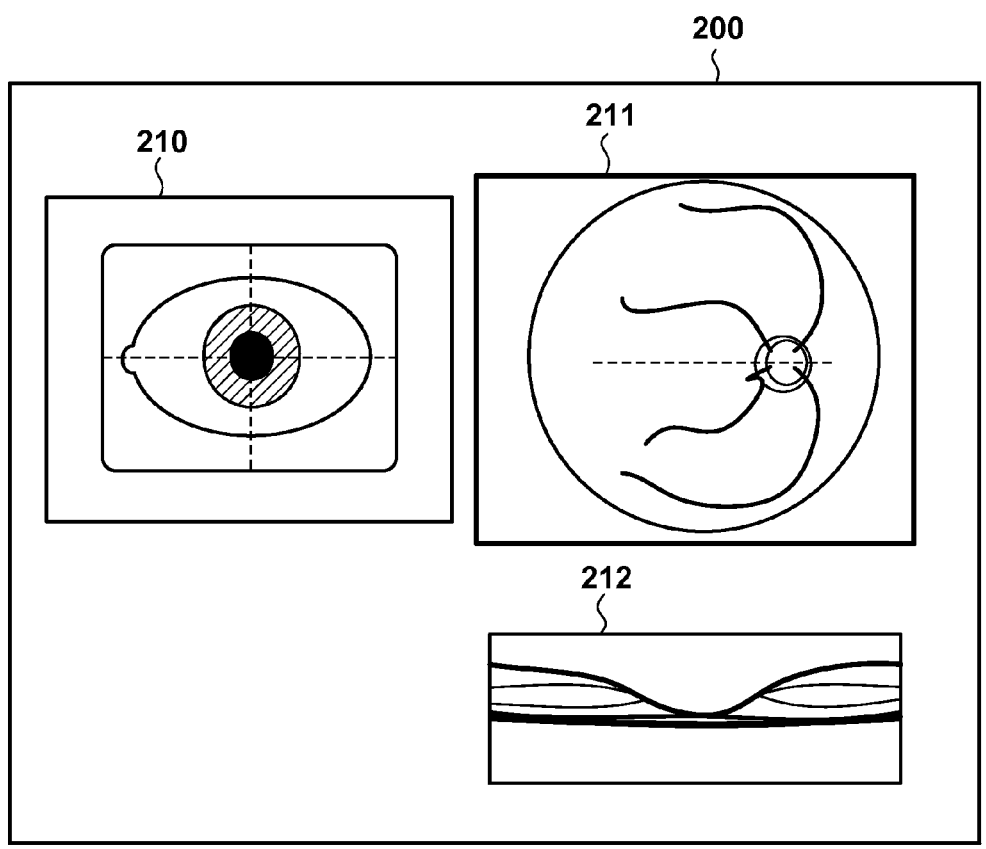
FIG. 7 shows images displayed on a monitor.

In step S5, a focus position is adjusted. A user adjusts the lens 101-1 while viewing the contrast and granularity of a tomographic image displayed on the monitor. FIG. 7 shows monitor display at the time of focus adjustment and OCT imaging by the user. A monitor 200 displays an anterior ocular image 210, a frontal fundus image 211, and a tomographic image 212. The displayed anterior ocular image 210 is obtained by processing the output from the infrared CCD 142. The frontal fundus image obtained in step S3 is displayed as the frontal fundus image 211. The tomographic image 212 is composed as a result of applying the above-described processing to the output from the line sensor 184.

<Handling for Dynamic Change 1 (Involuntary Fine Motion of Examined Eye)>

At the time of preview (from step S5 to step S7), the state of the frontal fundus image may change due to an involuntary fine motion and eye floaters of the examined eye of the examinee. In step S6, a display control unit (not shown) of the optical coherence tomography apparatus detects and extracts a dynamic change in the fundus based on a frontal fundus image obtained during display of the preview, and reflects the dynamic change in the frontal fundus image on a preview screen in real time. During display of the preview, the optical coherence tomography apparatus performs the scan with the X scanner 122-1 and the Y scanner 122-2 at a speed higher than the speed at the time of the main OCT measurement (S7) so as to detect an involuntary fine motion of the examined eye. As a result, the number of A-scan images obtained in a single measurement is small compared to the case of the main OCT measurement. At certain time t, the optical coherence tomography apparatus extracts the optic disc and a blood vessel pattern as characteristic points from the frontal fundus image. In the next frame t+1 also, the optical coherence tomography apparatus similarly extracts characteristic points from a fundus image, and calculates the amount of movement of the characteristic points from pixel positions in the frontal fundus image. The amounts of movements of characteristic points are calculated successively for t+2 onward. Based on the amounts of movements of characteristic points, the optical coherence tomography apparatus selects a display area of the frontal fundus image 211 from the frontal fundus image obtained in step S3; in this way, the user can check an involuntary fine motion of the examined eye in real time on the monitor.

<Handling for Dynamic Change 2: Eye Floaters>

In addition to an eyeball movement, such as an involuntary fine motion of the examined eye, eye floaters and other substances that move within the eye with time can be thought of as the causes of a dynamic change in a frontal fundus image (a fundus image). Eye floaters are caused by, for example, opacification of the vitreous body and detachment of the posterior vitreous body from the retina with aging. A fundus image shows floaters differently depending on exposure to light. The optical coherence tomography apparatus extracts only moving substances, typically eye floaters, from a fundus image and superimposes the extracted moving substances over the displayed frontal fundus image 211 using the following two methods. The first method is to extract a moving substance through inter-frame comparison of frontal fundus images that are obtained by the optical coherence tomography apparatus during the preview. The optical coherence tomography apparatus positionally matches a fundus image of time t with a fundus image of the next frame t+1 based on the above-described movements of characteristic points, and then detects a difference therebetween. As this difference can be thought of as a moving substance, the optical coherence tomography apparatus superimposes the difference over the displayed frontal fundus image 211. In the second method, the optical coherence tomography apparatus compares the frontal fundus image obtained in step S3 with a frontal fundus image that is obtained in real time, and extracts a difference therebetween as a moving substance.

<Handling for Dynamic Change 3: Blink Detection>

When the examinee has blinked, the optical coherence tomography apparatus notifies the examiner of the state of blinking by darkening a frontal fundus image on the monitor. Blink detection is performed to prevent a measurement error. By performing the OCT measurement while confirming that the examinee is opening his/her eye, the user can reduce the possibility of reduced throughput caused by re-imaging. When the examinee blinks, the line sensor 184 receives only the reference light. It is said that a time period generally required for a human to blink is approximately 0.1 to 0.15 seconds. As a result, in the obtained tomographic image and frontal fundus image, a region of A-scan images yielded by performing the scan during that time period is darkened. The optical coherence tomography apparatus determines that the examinee has blinked if the number of pixels having luminances lower than a preset threshold is larger than a preset threshold in the tomographic image or the frontal fundus image. The optical coherence tomography apparatus may notify the user of detection of blinking by displaying the word "blinking" and the like on the frontal fundus image 211 in addition to darkening the frontal fundus image 211. Any other display method may be used as long as it can notify the user of detection of blinking.

<Detection of Vignetting Caused by Pupil and Eyelashes>

Other than blinking, vignetting caused by the pupil and eyelashes also block measurement light that should irradiate the examined eye and prohibit the optical coherence tomography apparatus from obtaining an interference signal. The optical coherence tomography apparatus identifies the occurrence of vignetting caused by the pupil or eyelashes when, within a frontal fundus image obtained during the preview, luminance equal to or lower than a preset threshold is present in a region in the vicinity of the preset upper, lower, left, and right ends. The optical coherence tomography apparatus can notify the user of the occurrence of vignetting by extracting a vignetting region based on position information of pixels in the frontal fundus image and superimposing the vignetting region over the displayed frontal fundus image 211. Any other display method may be used as long as it can notify the user of detection of vignetting.

<Determination about Tomographic Image Based on Coherence Gate Position>

In step S7, the optical coherence tomography apparatus decides on a segment to be measured and performs the main OCT measurement. Then, in step S8, the optical coherence tomography apparatus determines the sensitivity of the tomographic image. As stated earlier, if the B-scan width is large at the time of OCT imaging, the sensitivity of a site of interest (the macula and the optic disc) in the tomographic image could possibly decrease due to the influence of the roll-off characteristics. In view of this, if the distance from the coherence gate position to the boundary portion between the vitreous body and the retina, which is calculated based on a tomographic image obtained in step S8, is larger than a threshold, the optical coherence tomography apparatus notifies the user of the possibility of a reduction in the sensitivity of the tomographic image by displaying an alert on the frontal fundus image 211 (step S9). For example, a "Low Quality" mark is displayed on a tomographic image in the vitreous body mode.

According to the above-described embodiment, with the use of a frontal fundus image obtained in the choroid mode, the examiner can perform imaging to produce a tomographic image while viewing a favorable frontal fundus image in the vitreous body mode. While the present embodiment has been described with a focus on the examined eye, the scan may be performed with respect to a human skin, a human organ, and other objects in addition to the examined eye, and the present invention is also applicable to an endoscope and other imaging apparatuses in addition to an ophthalmic imaging apparatus.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-093168, filed Apr. 28, 2014, which is hereby incorporated by reference herein in its entirety.

What is claimed is:

1. An ophthalmic imaging apparatus, comprising:
an imaging unit configured to perform imaging to produce a tomographic image of a fundus of an examined eye based on interference light obtained by combining measurement light and reference light in a vitreous body mode or in a choroid mode, wherein the imaging unit sets, in the vitreous body mode, a position in which an optical path length of the measurement light and an optical path length of the reference light match at a vitreous body side of the examined eye, and sets, in the choroid mode, the position at a choroid side of the examined eye;
a determination unit configured to determine whether aliasing has occurred in the tomographic image imaged in the vitreous body mode;
a movement unit configured to, when the determination unit has determined that the aliasing has occurred, move the position from the vitreous body side to the choroid side;
a generation unit configured to generate a fundus image based on a plurality of tomographic images having been produced through imaging performed by the imaging unit in the choroid mode; and
a display control unit configured to display, on a display unit, (a) the tomographic image imaged in the vitreous body mode and (b) the fundus image generated based on the plurality of tomographic images imaged in the choroid mode.

2. The ophthalmic imaging apparatus according to claim 1, wherein the movement unit moves the position by a distance that is equal to a sum of a distance from a current position to an outer boundary portion of a choroid in the tomographic image and a predetermined margin.

3. The ophthalmic imaging apparatus according to claim 1, wherein after the tomographic image has been produced through imaging performed by the imaging unit in a state where the position is at the choroid side, the movement unit moves the position to the vitreous body side.

4. The ophthalmic imaging apparatus according to claim 3, wherein the movement unit moves the position by a distance that is equal to a sum of a distance from a current position to a boundary portion between a vitreous body and a retina in the tomographic image and a predetermined margin.

5. The ophthalmic imaging apparatus according to claim 1, further comprising:
an obtainment unit configured to obtain a movement of the examined eye after the position has been moved by the movement unit to the vitreous body side; and
a decision unit configured to, based on the movement of the examined eye obtained by the obtainment unit, decide on a range to be displayed on the display unit from within the fundus image,
wherein the display control unit displays, on the display unit, the range within the fundus image that has been decided on by the decision unit.

6. The ophthalmic imaging apparatus according to claim 5, wherein the range within the fundus image that is displayed on the display unit as a result of the decision by the decision unit is smaller than a range of the fundus image generated by the generation unit.

7. The ophthalmic imaging apparatus according to claim 5, further comprising:
a detection unit configured to, after the position has been moved by the movement unit to the vitreous body side, detect a substance that is included in the examined eye and moves with time,
wherein the display control unit displays the substance detected by the detection unit on the display unit together with the fundus image.

8. The ophthalmic imaging apparatus according to claim 1, further comprising:
a blink detection unit configured to, after the position has been moved by the movement unit to the vitreous body side, detect blinking of the examined eye,
wherein when the blink detection unit has detected the blinking, the display control unit displays the detection of the blinking on the display unit.

9. The ophthalmic imaging apparatus according to claim 1, further comprising:
a vignetting detection unit configured to, after the position has been moved by the movement unit to the vitreous body side, detect vignetting of the measurement light caused by a pupil or an eyelash of the examined eye,
wherein when the vignetting detection unit has detected the vignetting of the measurement light, the display control unit displays the detection of the vignetting of the measurement light on the display unit.

10. An ophthalmic imaging apparatus, comprising:
an imaging unit configured to perform imaging to produce a tomographic image of a fundus of an examined eye based on interference light obtained by combining measurement light and reference light in a vitreous body mode or in a choroid mode, wherein the imaging unit sets, in the vitreous body mode, a position in which an optical path length of the measurement light and an optical path length of the reference light match at a vitreous body side of the examined eye, and sets, in the choroid mode, the position at a choroid side of the examined eye;
a movement unit configured to move the position from the vitreous body side to the choroid side;
a generation unit configured to generate a fundus image based on a plurality of tomographic images having been produced through imaging performed by the imaging unit in the choroid mode; and
a display control unit configured to display, on a display unit, (a) the tomographic image imaged in the vitreous body mode and (b) the fundus image generated based on the plurality of tomographic images imaged in the choroid mode.

11. The ophthalmic imaging apparatus according to claim 10, wherein the movement unit moves the position by a distance that is equal to a sum of a distance from a current position to an outer boundary portion of a choroid in the tomographic image and a predetermined margin.

12. The ophthalmic imaging apparatus according to claim 11, wherein after the tomographic image has been produced through imaging performed by the imaging unit in a state where the position is at the choroid side, the movement unit moves the position to the vitreous body side.

13. The ophthalmic imaging apparatus according to claim 12, wherein the movement unit moves the position by a distance that is equal to a sum of a distance from a current position to a boundary portion between a vitreous body and a retina in the tomographic image and a predetermined margin.

14. The ophthalmic imaging apparatus according to claim 10, further comprising:
an obtainment unit configured to obtain a movement of the examined eye after the position has been moved by the movement unit to the vitreous body side; and
a decision unit configured to, based on the movement of the examined eye obtained by the obtainment unit, decide on a range to be displayed on the display unit from within the fundus image,
wherein the display control unit displays, on the display unit, the range within the fundus image that has been decided on by the decision unit.

15. The ophthalmic imaging apparatus according to claim 14, wherein the range within the fundus image that is displayed on the display unit as a result of the decision by the decision unit is smaller than a range of the fundus image generated by the generation unit.

16. The ophthalmic imaging apparatus according to claim 10, further comprising:
a detection unit configured to, after the position has been moved by the movement unit to the vitreous body side, detect a substance that is included in the examined eye and moves with time,
wherein the display control unit displays the substance detected by the detection unit on the display unit together with the fundus image.

17. The ophthalmic imaging apparatus according to claim 10, further comprising:
a blink detection unit configured to, after the position has been moved by the movement unit to the vitreous body side, detect blinking of the examined eye,
wherein when the blink detection unit has detected the blinking, the display control unit displays the detection of the blinking on the display unit.

18. The ophthalmic imaging apparatus according to claim 10, further comprising:
a vignetting detection unit configured to, after the position has been moved by the movement unit to the vitreous body side, detect vignetting of the measurement light caused by a pupil or an eyelash of the examined eye,
wherein when the vignetting detection unit has detected the vignetting of the measurement light, the display control unit displays the detection of the vignetting of the measurement light on the display unit.

19. A control method for an ophthalmic imaging apparatus, the control method comprising:

an imaging step of performing imaging to produce a tomographic image of a fundus of an examined eye based on interference light obtained by combining measurement light and reference light in a vitreous body mode or in a choroid mode, wherein the ophthalmic imaging apparatus sets, in the vitreous body mode, a position in which an optical path length of the measurement light and an optical path length of the reference light match at a vitreous body side of the examined eye, and sets, in the choroid mode, the position at a choroid side of the examined eye;

a determination step of determining whether aliasing has occurred in the tomographic image imaged in the vitreous body mode;

a movement step of, when the determination step has determined that the aliasing has occurred, moving the position from the vitreous body side to the choroid side;

a generation step of generating a fundus image based on a plurality of tomographic images having been produced through imaging performed in the imaging step in the choroid mode; and a display control step of displaying, on a display unit, (a) the tomographic image imaged in the vitreous body mode and (b) the fundus image generated based on the plurality of tomographic images imaged in the choroid mode.

20. A non-transitory computer-readable storage medium storing a computer program for controlling a computer to execute the control method according to claim 19.

21. A control method for an ophthalmic imaging apparatus, the control method comprising:

an imaging step of performing imaging to produce a tomographic image of a fundus of an examined eye based on interference light obtained by combining measurement light and reference light in a vitreous body mode or in a choroid mode, wherein the ophthalmic imaging apparatus sets, in the vitreous body mode, a position in which an optical path length of the measurement light and an optical path length of the reference light match at a vitreous body side of the examined eye, and sets, in the choroid mode, the position at a choroid side of the examined eye;

a movement step of moving the position from the vitreous body side to the choroid side;

a generation step of generating a fundus image based on a plurality of tomographic images having been produced through imaging performed in the imaging step in the choroid mode; and a display control step of displaying, on a display unit, (a) the tomographic image imaged in the vitreous body mode and (b) the fundus image generated based on the plurality of tomographic images imaged in the choroid mode.

22. A non-transitory computer-readable storage medium storing a computer program for controlling a computer to execute the control method according to claim 21.

* * * * *